United States Patent
Tsubouchi et al.

(10) Patent No.: US 6,815,427 B2
(45) Date of Patent: Nov. 9, 2004

(54) SERICIN-CONTAINING MATERIAL, PROCESS FOR PRODUCING THE SAME METHOD OF USING THE SAME

(75) Inventors: Kozo Tsubouchi, Ibaraki (JP); Hiromi Yamada, Tsukuba (JP); Yoko Takasu, Tsukuba (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 319 days.

(21) Appl. No.: 10/169,042

(22) PCT Filed: Mar. 22, 2001

(86) PCT No.: PCT/JP01/02250

§ 371 (c)(1),
(2), (4) Date: Jun. 24, 2002

(87) PCT Pub. No.: WO02/34885

PCT Pub. Date: May 2, 2002

(65) Prior Publication Data

US 2003/0087433 A1 May 8, 2003

(30) Foreign Application Priority Data

Oct. 24, 2000 (JP) ........................................ 2000-324034

(51) Int. Cl.⁷ .......................... C12N 5/00; C07K 14/78; A61K 7/00; A61K 9/14; A61L 15/20
(52) U.S. Cl. .......................... 514/21; 435/68.1; 435/69; 435/325; 435/391; 435/402; 530/353; 264/202; 424/69; 424/70.14; 424/401; 424/445; 514/2; 514/12
(58) Field of Search ................... 435/325, 391, 435/68.1, 69; 530/353; 514/12, 21, 2; 424/401, 445, 69, 70.14; 264/202

(56) References Cited

U.S. PATENT DOCUMENTS 6,175,053 B1   1/2001   Tsubouchi

FOREIGN PATENT DOCUMENTS

| JP | 64-055191 | 3/1989 |
| JP | 08-268905 | 10/1996 |
| JP | 11-092564 | 4/1999 |
| JP | 11-152206 | 6/1999 |
| JP | 11-243948 | 9/1999 |
| WO | WO 98/57676 | 12/1998 |

OTHER PUBLICATIONS

JPAB Abstract JP404053490 Asakura et al Feb. 21, 1992.*
JPAB Abstract JP02000191446 Suzuki et al Jul. 11, 2000.*
JPAB Abstract JP02003165843 Hasegawa et al Jun. 10, 2003.*
Voegeli, R., "Sericin no Hifu Hohitsu, Kou Shiwa Kouka", Fragrance Journal, vol. 26, (1998), No. 4, pp. 70–74. (With English abstract).

* cited by examiner

Primary Examiner—Herbert J. Lilling
(74) Attorney, Agent, or Firm—Flynn, Thiel, Boutell & Tanis, P.C.

(57) ABSTRACT

The object of the present invention is to elucidate a biologically active function of a component constituting undegraded sericin and to provide a novel medical material, cosmetic material, etc. utilizing the functional composition. Disclosed is a cell growth promoter obtainable by elution from a fiber discharged by a domestic silkworm, e.g., cocoon filaments or the like, wherein the cell growth promoter comprises sericin having a molecular weight of about 400,000 as measured by sodium dodecyl sulfate-polyacrylamide gel electrophoresis (SDS-PAGE) as a main component. This cell growth promoting agent (substance) is extremely useful because growth of cells is promoted when it is used in a wound dressing material, a vascular endothelium forming material and an organ forming material for medical use, in a cell culture base material for biological use, or in a cosmetic material for skin care use.

10 Claims, 5 Drawing Sheets

FIG. 1

SDS-PAGE of cocoon filament proteins

Cocoon filament protein (R) reduced with 2-mercaptoethanol and
non-reduced cocoon filament protein (N)
- s: Sericin
- f: Fibroin
- M: Marker

FIG. 2

SDS-PAGE of eleven fractions resulting from addition of ethanol to a cocoon filament protein solution fH, fL: Fibroin components
s-a, s-d, s-b, s-c: Sericin components
M: Marker

FIG. 3

SDS-PAGE of three major components (s-a, s-d, s-b) of sericin fractionated and purified

M: Marker

FIG. 4

M: Marker
fH: Fibroin

FIG. 5

M: Marker

SERICIN-CONTAINING MATERIAL, PROCESS FOR PRODUCING THE SAME METHOD OF USING THE SAME

TECHNICAL FIELD

The present invention relates to a cell growth promoter containing domestic silkworm sericin, and particularly to a medical material, a cell culture bed material and a cosmetic material.

Further, the present invention relates to a method for obtaining sericin having a function of growing cells from fibers discharged by domestic silkworms, e.g., cocoon filaments or the like.

BACKGROUND ART

Fibers discharged by domestic silkworms, e.g., cocoon filaments or the like, comprise two kinds of proteins, fibroin and sericin. Sericin is present while coat fibroin.

Cocoons are subjected to steps including drying, boiling, thread reeling, etc., followed by degumming (sericin remouing) The silk filaments degummed (fibroin fibers) have been used as silk fabrics.

Further, silk yarn is the only long fiber of the natural fiber and has excellent crystallinity and high strength. Thus, the silk yarn has been used, since old times, also as a thread for operations as well as clothes.

In recent years, silk protein has attracted much attention to its inherent functions and, as a result, has come to be used actively for various applications.

In development of new materials using silk protein, fibroin preceded sericin. In recent years, however, sericin, which is another silk protein, has also become a subject of research and development based on the achievements with respect to fibroin.

For example, there are reports on a cosmetic powder comprising a base the surface of which has been covered with a hydrolysate of sericin (JP-A-10-226626), a cosmetic containing cellulose fiber impregnated with a fibroin dispersion and/or an aqueous sericin solution (JP-A-11-152206), a skin irritation inhibitor containing a sericin hydrolysate as an active component (JP-A-10-245345), a collagen production promoter and a skin preparation for external use for prevention from getting older, both containing a sericin hydrolysate as an active component (JP-A-10-226653), a skin preparation for external use containing a sericin hydrolysate and a degradation product of yeast (JP-A-11-193210) and a cell culture bed comprising a film made up of silk protein(s) (fibroin and/or sericin) of domestic silkworms (Minoura et al., Attachment and growth of cultured fibroblast cells on Silk protein matrices, J. Biomedical Materials Res., Vol.29, 1215-1221(1995)).

On the other hand, when a conventional method in which sericin is recovered from a degumming waste liquor is used as a method for obtaining sericin from cocoon filaments or the like, only products having a low molecular weight such as an average molecular weight of 50,000 or less can be obtained (JP-A-1-168906, JP-A-4-202435, etc.)

In short, since sericin in cocoon filaments are crystallize, it hardly dissolves in water. It, however, has been removed by being degraded in hot alkaline water.

Sericin having a high molecular weight such as an average molecular weight of 100,000 or more has recently become to be obtained efficiently (JP-A-11-92564, JP-A-11-131318, etc.) and a method has been developed in which sericin and the like are eluted from cocoon filaments or the like so that the reduction of molecular weight is controlled (JP-A-11-228837, JP-2000-38514, etc.)

Sericin in domestic silkworms has long been said to be a mixture of proteins having molecular weights of from several tens of thousands to hundreds of thousands. Since it is huge and, therefore, easily forms aggregate or becomes insoluble, it is difficult to handle.

For this reason, the problem that of what types of protein components the fractionation and purification in an undegraded state are constituted has been left unsolved.

Further, in most of the conventional reports in which functions such as a physiological activity are suggested, reduction in molecular weight takes place in an extraction step.

Since we have recently succeeded in extracting and fractionating undegraded sericin, the research of application of these components fractionated has become a main issue.

The object of the present invention is to examine the physiological activities of the components constituting undegraded sericin and to provide new medical materials, cosmetic materials and the like utilizing such functional components.

DISCLOSURE OF THE INVENTION

Means for Solving Problem

For solving the above-described problems, the present inventors first researched the relation between the molecular weight and physiological activity of sericin constituting undegraded sericin. As a result, they obtained information that, of the components constituting undegraded sericin, a sericin having a specific molecular weight has an extremely high cell growth promoting action.

The present invention has been created based on the above information and comprises the following compositions:

Namely, the present invention is present in (1) a cell growth promoter obtainable by elution from a fiber discharged (cocoon filaments or the like) wherein the cell growth promoter comprises sericin having a molecular weight of about 400,000 as measured by sodium dodecyl sulfate-polyacrylamide gel electrophoresis (SDS-PAGE) as a main component.

The present invention is present also in (2) a method comprising dissolving sericin contained in a fiber discharged by a domestic silkworm (cocoon filaments or the like) in an aqueous urea solution, and then separating and recovering sericin having a molecular weight of about 400,000 as measured by sodium dodecyl sulfate-polyacrylamide gel electrophoresis (SDS-PAGE).

The present invention is present also in (3) the method for separating and recovering according to claim 2, wherein sericin is dissolved in an aqueous urea solution of a concentration of 4 M or more.

Further, the present invention is present also in (4) a cell growth promoter obtainable by dissolving a fiber discharged by a domestic silkworm (cocoon filaments or the like) in an aqueous solution of a neutral salt, wherein the cell growth promoter contains silk fibroin and sericin having a molecular weight of about 400,000 as measured by sodium dodecyl sulfate-polyacrylamide gel electrophoresis (SDS-PAGE).

Further, the present invention is present also in (5) a cell growth promoter, wherein the cell growth promoter is in the form of a powder or a film.

Further, the present invention is present also in (6) a cell growth promoter obtainable by degumming a fiber discharged by a domestic silkworm (cocoon filaments or the like) under mild conditions and removing sericin having low molecular weight, wherein the cell growth promoter comprises a fibrous material in a state where the surface of a fibroin filament is covered with a sericin component having a molecular weight of about 400,000 as measured by sodium dodecyl sulfate-polyacrylamide gel electrophoresis (SDS-PAGE).

Further, the present invention is present also in (7) a method for producing a fibrous material in a state where the surface of a fibroin filament is covered with a sericin component having a molecular weight of about 400,000 as measured by sodium dodecyl sulfate-polyacrylamide gel electrophoresis (SDS-PAGE), the method comprising degumming a fiber discharged by a domestic silkworm (cocoon filaments or the like) under mild conditions and removing sericin having low molecular weight.

Further, the present invention is present also in (8) a method for producing a fibrous material, wherein scouring by boiling is conducted within mild pH range as close to neutrality as possible.

Further, the present invention is present also in (9) a cell growth promoter obtainable by immersing a liquid silk contained in the middle silk gland and the anterior silk gland in the body of a silkworm, wherein the cell growth promoter comprises sericin having a molecular weight of about 400,000 as measured by sodium dodecyl sulfate-polyacrylamide gel electrophoresis (SDS-PAGE) as a substantial main component.

Further, the present invention is present also in (10) a method of using the cell growth promoter described above for a cosmetic material as a skin care material; a wound dressing material, a material for vascular endothelium formation and a material for organ formation as medical materials; and a cell culture bed material as a biological material.

MODE FOR CARRYING OUT THE INVENTION (1) Separation and Identification of Various Types of Sericins Constituting Undegraded Sericin (a) Obtainment of Undegraded Sericin Since the use of conventional elution methods using an acidic or alkaline aqueous solution or enzymatic treatment as means for isolating sericin of cocoon filaments or the like results in reduction of molecular weight caused by hydrolysis, these elution methods cannot be adopted.

Therefore, a silk protein solution comprising fibroin and sericin is prepared by dissolving cocoon filaments or the like together with fibroin in an aqueous solution of a neutral salt such as lithium thiocyanate.

By such a dissolution method using an aqueous solution of a neutral salt, a silk protein solution containing approximately undegraded sericin can be obtained with inhibition of molecular weight reduction caused by hydrolysis. The resulting silk protein solution containing undegraded sericin is then subjected to measurement of molecular weight and separation of sericin by means of sodium dodecyl sulfate-polyacrylamide gel electrophoresis (SDS-PAGE).

(Sodium dodecyl sulfate-polyacrylamide gel electrophoresis is hereinafter abbreviated SDS-PAGE.)

As a neutral salt used in the above-mentioned dissolution method using an aqueous solution of a neutral salt, lithium thiocyanate, lithium bromide, calcium chloride, calcium nitrate and the like can be mentioned, and particularly, lithium thiocyanate and lithium bromide are preferred.

Cocoon filaments or the like are added into a concentrated aqueous solution of a neutral salt and dissolved.

During the dissolution, mild conditions are selected for the purpose of inhibiting reduction of the molecular weight of silk protein as much as possible.

The neutral salt is used in a concentration of 50% saturation or more. The heating temperature is set within the range of from room temperature to 80 (° C.).

Since reduction of the molecular weight will occur if the temperature exceeds 80 (° C.), the temperature is preferably as low as possible considering the dissolution time and the type of the neutral salt.

The dissolution time is determined within the range of from 1 to 20 minutes so that the cocoon filament can be dissolved completely and no reduction of molecular weight occurs in consideration of conditions such as the type of the neutral salt, temperature and the like.

The neutral salt solution containing silk protein dissolved is subjected to dialysis to form a pure aqueous solution of silk protein.

(b) Measurement of Molecular Weight by Electrophoresis

Silk protein is separate by electrophoresis into two components of fibroin (H and L) and four components of sericin (a, b, c and d).

A solution obtained by dissolving cocoon filaments or the like in the aforementioned aqueous neutral salt solution and replacing with a 5 M (5 mol/l) urea solution is treated with a reducing agent, e.g., 2-mercaptoethanol (ME) to break crosslinking bonds (S—S bonds of proteins).

The resultant is subjected to SDS-PAGE to measure the molecular weight of each protein component constituting cocoon filaments.

The measurement by electrophoresis revealed that sericin a having a molecular weight of about 400,000, sericin d having a molecular weight of about 250,000, sericin b having a molecular weight of about 200,000 and sericin c having a molecular weight of about 35,000 account, respectively, for about 45%, about 34%, about 15.5% and about 5.3% of the cocoon layer sericin.

(2) Preparation of a Material Comprising Sericin a Component

Sericin a component is eluted by heating cocoon filaments or the like in an aqueous urea solution under atmospheric pressure.

The aqueous urea solution has a concentration of 4 M or more, preferably from 7 M to saturation and is kept at from 70 to 100° C. for a period of from 3 to 30 minutes preferably from 5 to 30 minutes to extract sericin.

The lower the concentration of the aqueous urea solution is the better, because the lower the concentration of the aqueous urea solution is, the less the amount of the urea and the lower the cost.

However, if the concentration of urea is low, dissolution, in particular, of sericin a is reduced and the amount of sericin a extracted is reduced. Therefore, it is recommended to set the concentration of urea to 4 M or more in order to achieve rapid extraction and a great amount of sericin a recovered.

If the heating temperature is low, it is difficult for sericin to be extracted, whereas a high heating temperature results in degradation of sericin and reduction in molecular weight.

If the extraction time is short, it is difficult for sericin to be extracted, whereas if long, sericin is degraded.

Addition of 1% or more of a reducing agent, e.g., ME, to the aqueous urea solution can increase the recovery rate of sericin.

To the solution of sericin obtained in the manner mentioned above is added an organic solvent, e.g., methanol, ethanol and acetone, in a volume of from 3 to 5 times, thereby obtaining a precipitate of undegraded sericin.

The resultant is dissolved in an aqueous solution of a neutral salt such as lithium thiocyanate containing 1% or more of a reducing agent, e.g., ME or the like, and then organic solvents such as ethanol are added one after another to form a precipitate, which is fractionated into various types of sericins while being checked by SDS-PAGE.

A silk protein having a sericin a content of 90% or more is obtained through repetition of operations comprising dissolution and precipitation of a precipitate.

Alternatively, a silk protein having a sericin a content of 90% or more is obtained by treatment, using a reducing agent (e.g., ME or the like), of a silk protein solution containing fibroin obtained by dissolving cocoon filaments or the like in an aqueous solution of a neutral salt, e.g., lithiumthiocyanate, followed by fractionation of silk protein components by repeating precipitation with an organic solvent such as ethanol and dissolution with an aqueous solution of lithium thiocyanate containing ME.

The sericin a purified through the repetition of dissolution and precipitation is dissolved in an aqueous solution of a neutral salt such as lithium thiocyanate and then desalted by dialysis or the like.

The aqueous solution of the sericin a purified and desalted is spray dried to yield a powdery material.

Further, the aqueous solution of the sericin a purified and desalted is dried on a flat plate to yield a film-like material.

The film-like material may be pulverized into a powdery material.

The above-obtained powdery or film-like material comprising sericin a component can be used, as the entire or a part, as a cell culture bed material, etc. for biological applications, as a wound dressing material, a material for vascular endothelium formation (artificial blood vessel), a material for forming an organ, etc. for medical applications, and as a cosmetic material for a skin care application.

If the powder has an average particle diameter is from 1 to 1,000 $\mu$m, preferably from 1 to 100 $\mu$m, it can follow the movement of the skin or the like flexibly and, therefore, can be used also as a wound dressing material.

(3) Preparation of a Material Comprising Sericin a and Fibroin

When a material containing sericin a is used especially as a film-like material, it is not necessarily desirable to use a material made up only of sericin a component as received for a wound dressing material or for a medical material, e.g., an artificial blood vessel because of its unsatisfactory strength.

If fibroin, which is another protein component constituting cocoon filaments and is constituted of silk yarn having both good biological compatibility and good strength, is used in combination with sericin a, a material more suitable for medical materials such as a wound dressing material and an artificial vessel can be obtained.

In an embodiment of the use of sericin a and fibroin in combination can be used an aqueous sericin a-fibroin mixed solution obtained by mixing an aqueous solution comprising sericin a and an aqueous fibroin solution prepared by dissolving silk yarn in an aqueous solution of a neutral salt such as a lithium salt.

As the aqueous neutral salt solution, a 5 M or more aqueous solution of lithium thiocyanate, preferably a saturated aqueous solution having a concentration of about 9 M is effective.

The more the amount, relative to a raw silk material, of a solvent, the easier the raw silk material is dissolved, but the more inefficient purification, desalting and the like become.

Thus, if the amount, relative to a raw silk material, of a solvent is reduced as much as possible, silk protein can be recovered efficiently.

For this reason, the amount of the aqueous neutral salt solution to a raw silk material is desirably at least 7 times, preferably from 9 to 50 times the amount of the raw silk material.

The desalting of a solution is carried out by dialysis against water.

Dialysis is carried out until no precipitate is formed from the extradialysis fluid by addition of $AgNO_3$.

Through this operation, an aqueous sericin a-fibroin mixed solution is obtained.

The aqueous mixed solution obtained is dried on a flat plate to form a film-like material.

When forming a film, it is desirable to carry out dialysis as quickly as possible, specifically, within three days, preferably within two days.

If dialysis takes many days, it becomes difficult to form a film because silk protein is caused to gel and become massive.

The aqueous silk protein solution is formed into a film by letting an aqueous silk protein solution flow on a plastic, especially acrylic, plate and drying it quickly so that the crystallinity becomes less than 10%.

For example, it is preferable to dry in a chamber of 60% RH (relative humidity) or less while sending air.

A film having a crystallinity of 10% or more has a poor water absorbability and, therefore, when put on a wound, it cannot absorb an exudate from the wound sufficiently and cannot become flexible. It, therefore, may damage the wound.

For this reason, it is not suitable for a wound dressing material.

A powdery material can be obtained by spray drying an aqueous sericin a-fibroin mixed solution desalted in advance, by freeze drying the aqueous mixed solution, or by precipitating with alcohol or the like, drying and then pulverizing.

It can be obtained also by pulverizing a film-like material.

Since the shape of the powder is different from a film, it can be used as a wound dressing material when the crystallinity of the powder is in the range of from 0 to 100%.

(4) Fibrous Material Comprising a Fibroin Fiber the Surface of which is Covered with Sericin a Component When a raw silk material such as cocoon filaments, etc. is degummed, sericin d and b, which are easy to be dissolved in water, are removed in a first stage. In a stage where about 40% of sericin has been removed, the surface of cocoon filaments is constituted almost of sericin a and, therefore, it is preferable to use raw silk obtained by completing the degumming at this stage.

When degumming a raw material such as cocoon filaments, etc. by boiling, the farther the pH of the degumming solution is away from neutrality, the easier it is to obtain sericin. However, in this case, since degradation occurs and the molecular weight is reduced, it is preferable to conduct degumming within a mild pH range as close to neutrality as possible.

When degumming is carried out using water, the degumming is carried out by immersing a raw material containing sericin a in water.

In this case, the higher the water temperature, the more efficient it is. To boil water under atmospheric pressure is effective.

For preventing molecular weight reduction, the boiling time is preferably several hours or shorter, more preferably one hour or shorter.

When degumming is carried out using a soap, a soap an aqueous solution of which shows pH of 10 or less, e.g., a marseilles soap having a concentration of 0.3% is used and the boiling is carried out for one hour or shorter, preferably for 30 minutes or shorter.

In materials comprising sericin a and fibroin, the content of sericin a is preferably 5% or more, more preferably 20% or more.

A fibrous material in which the surface of cocoon filaments is covered only with sericin a and which is obtained by degumming a raw silk material such as cocoon filaments or the like by the above-described method and removing sericins d and b, which are easy to be dissolved in water, may be used as medical materials, such as threads for operation, a wound dressing material and an artificial blood vessel, and cosmetic materials, as received or after being processed into woven fabric, nonwoven fabric or the like.

Alternatively, an aqueous silk protein solution is obtained by dissolving and desalting a fibrous material having a surface covered mainly with sericin a, in a method similar to that described in (1)(a) above.

By drying the resulting solution on a flat plate, a film-like material is obtained.

Alternatively, a powdery material is obtained by spray drying of the solution.

Further, a film-like material may be pulverized into a powdery material.

The above-obtained powdery or film-like material comprising sericin a can be used, as the entire or a part, as medical materials such as a wound dressing material and an artificial blood vessel or as a cosmetic material for skin care applications.

If the powder has an average particle diameter is from 1 to 1,000 $\mu$m, preferably from 1 to 100 $\mu$m, it can follow the movement of the skin or the like flexibly and, therefore, can be used also as a wound dressing material.

In the present invention, the cocoon filament or the like as a raw silk material used for obtaining sericin a (the purity is 90% or more) and a material containing sericin a is defined to be a substance containing cocoon filament sericin discharged by domestic silkworms.

The substance containing cocoon filament sericin includes undegummed materials such as cocoon layers of domestic silkworms, cocoon filaments, raw silk, woven or knitted silk fabrics, their incompletely degummed materials, and fibers, powders and films containing sericin. Of these materials, all of those containing sericin a can be used as a raw silk material.

Further, a cocoon of "sericin silkworm" which discharges only sericin containing no fibroin can also be used as a raw silk material.

(5) Sericin a from the Middle Silk Gland and the Anterior Silk Gland Liquid Silk in the Body of a Silkworm and a Material Containing Sericin a The silk gland of a domestic silkworm immediately before discharging silk is removed and is torn in water. The contents, that is, the liquid silk and the silk gland cells, are separated.

The silk gland is separated into the anterior portion, the middle portion and the posterior portion.

In the liquid silk contained in the anterior and middle silk glands, a liquid fibroin several millimeters in diameter is covered with liquid sericin of from 0.1 mm to 0.5 mm thickness.

Since both liquid fibroin and liquid sericin are soluble in water, a mixed aqueous solution containing sericin and fibroin can be obtained by immersing the liquid silk of the anterior and middle silk glands.

Since sericin is dissolved quicker, an aqueous solution containing much sericin can be obtained through 10 to 30-minute immersion. Prolongation of the immersion time results in increase of the ratio of fibroin.

If a method of spray dry is applied for this aqueous solution, a powder can be obtained.

Alternatively, a powder can be obtained also by freeze dry or precipitation using alcohol or the like, followed by drying and pulverization.

If drying the solution on a flat plate, a film can be obtained. A powder can be obtained by pulverizing the film.
(Effect)

The cell growth promoting agent (substance) according to the present invention that contains, as a main component, sericin having a molecular weight, as measured by SDS-PAGE, of about 400,000 obtained by being eluted from fibers discharged by domestic silkworms (e.g., cocoon filaments or the like) is a substance obtained by being eluted from the cocoon filaments or the like while being left almost undegraded. The cell growth promoter is a substantial active component for a cell growth promoting action that sericin constituting cocoon filaments or the like has.

Further, the cell growth promoting agent (substance) that contains, as a main component, sericin having a molecular weight, as measured by SDS-PAGE, of about 400,000 can also be obtained from a liquid silk.

The cell growth promoting agent (substance) has an action of promoting the growth of cells and, therefore, is extremely useful when used in a wound dressing material, a material for vascular endothelium formation and a material for forming an organ for medical applications, in a cell culture bed material for biological applications and a cosmetic material for skin care applications.

BEST MODE FOR CARRYING OUT THE INVENTION

For the purpose of showing the utility, in the above-mentioned applications, of the cell growth promoter of the present invention, experiments (examples) with respect thereto were carried out. These experiments will be described below.

The present invention is not restricted to these examples.

EXAMPLE 1

[Fractionation and Purification of Sericin a]

Using, as a raw silk material, a domestic silkworm cocoon within one month from discharge of silk, not treated with light, heat, water or the like, a cocoon layer was dissolved in an about 70% (% by weight) aqueous LiSCN (pH 7) solution, thereby yielding a silk protein solution having a concentration of about 5%.

Figure 1:
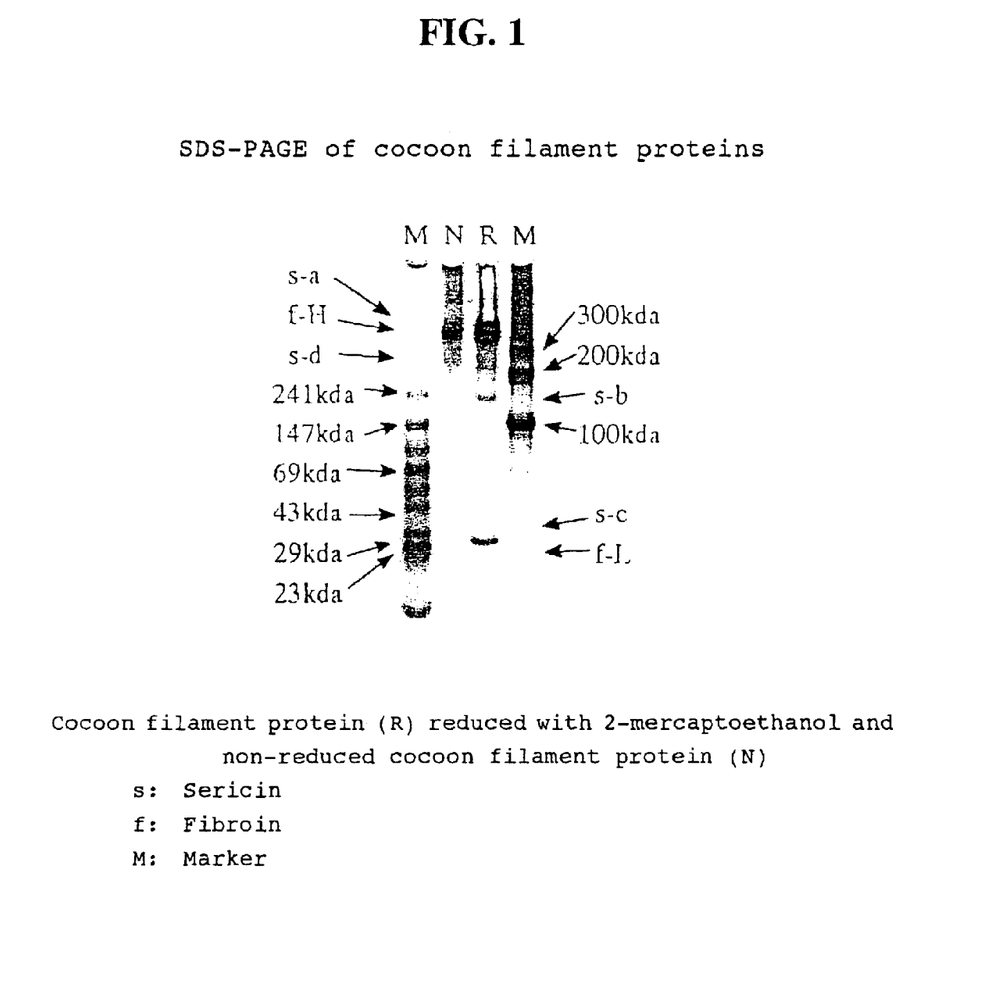
FIG. 1 is SDS-PAGE of cocoon filament proteins.

FIG. 1 shows SDS-PAGEs (2–15% gradient gel) of a sample (N) obtained by replacing the solvent of the above silk protein solution by a 5 M aqueous urea solution and a sample (R) obtained by adding 1% 2-mercaptoethanol (ME) to the sample (N) to break an SS bond.

FIG. 1 is SDS-PAGE of cocoon filament proteins.

A cocoon filament protein reduced with 2-mercaptoethanol is symbolized by (R) and a cocoon filament protein not reduced is symbolized by (N).

Sericin, fibroin and a marker are symbolized by (s), (f) and (M), respectively.

A cocoon filament protein comprises fibroin and sericin. By breaking an SS bond, fibroin is divided into two components [H(fibroin H chain and fibroin L chain)] and sericin is divided into four components (a, b, c and d). These can be considered to be main components of silk protein.

Each component of silk protein was estimated from the dyeing concentration of the bonds of R in FIG. 1.

The results are shown in Table 1.

TABLE 1

Ratios of components of sericin

| Component | Ratio |
|---|---|
| s-a | 45.0 |
| s-d | 34.2 |
| s-b | 15.5 |
| Others | 5.3 |

In sericin, components a and d are contained in particularly much amounts. Since three components a, b and d account for about 95%, these three components are defined as major components of sericin.

Subsequently, to 10 ml of a solution obtained by reducing the above-described 5% silk protein solution with ME, 82 ml of ethyl alcohol was added one after another in eleven portions.

After each addition, a precipitate formed was centrifugally separated and recovered.

Figure 2:
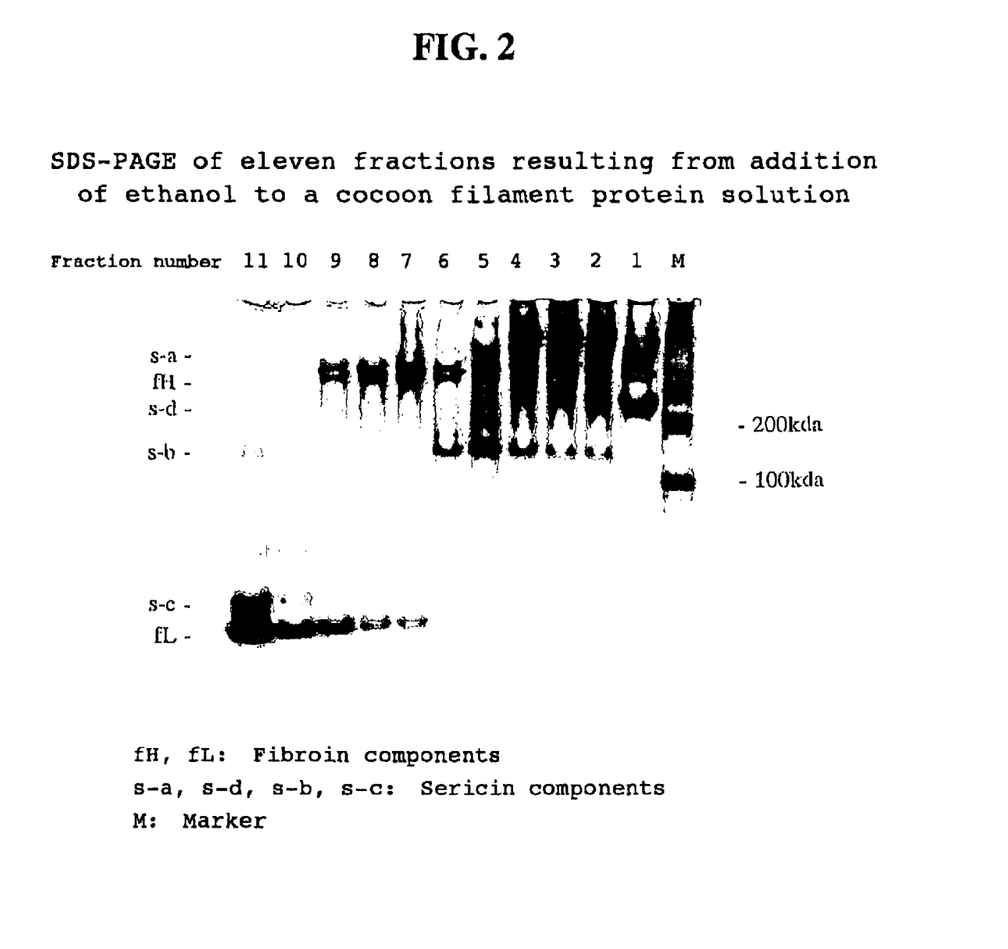
FIG. 2 is SDS-PAGE of precipitates.

The SDS-PAGE of each precipitate is shown in FIG. 2.

FIG. 2 is SDS-PAGE of eleven fractions obtained by addition of ethanol to a silk filament protein solution.

In FIG. 2, it is found that sericin d is present in the first and second precipitates, sericin a is present in the second through fifth precipitates, sericin b is present in the second through sixth precipitates, and sericin c is present in the tenth and eleventh precipitates. For obtaining the three major components of sericin in purities as high as possible, the first, third, fourth and fifth precipitates were redissolved separately in 70% aqueous lithium thiocyanate solutions (pH 7) containing 1% ME and were reprecipitated by adding ethanol.

Figure 3:
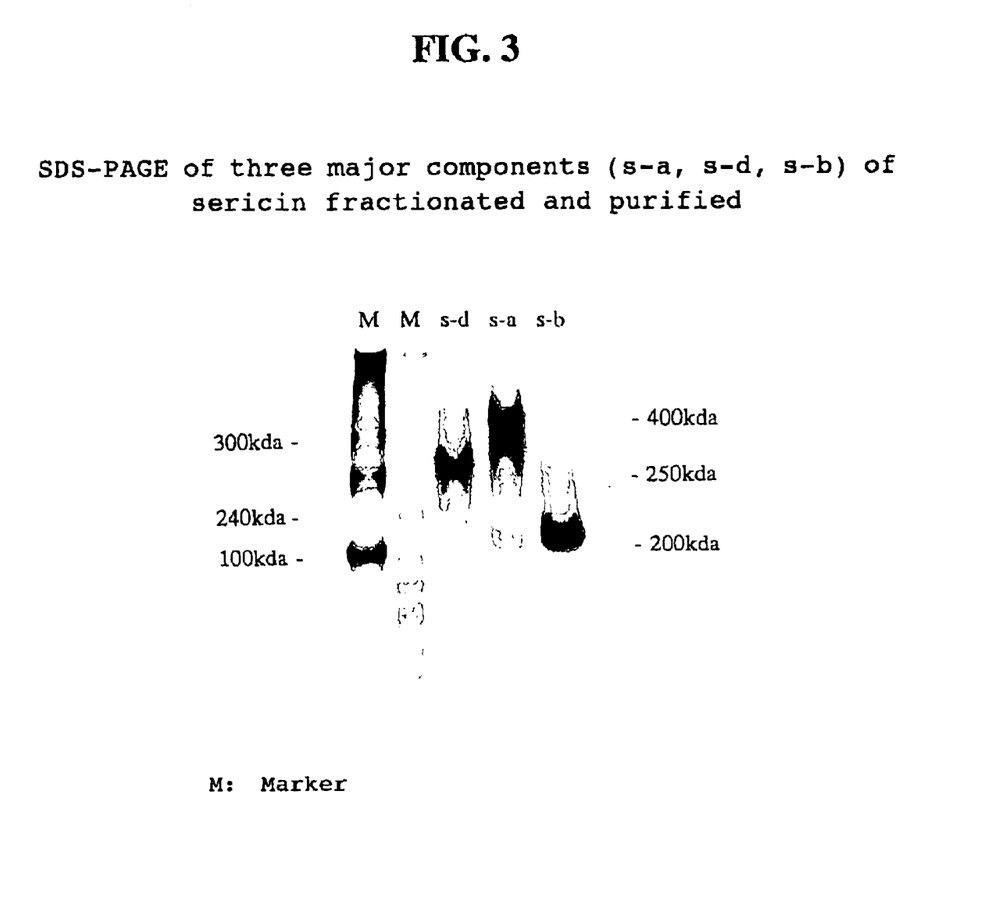
FIG. 3 is SDS-PAGE of three major components (s-d, s-a, s-b) of sericin fractionated and purified.

Of the precipitates obtained, SDS-PAGEs of sericins d, a and b are shown in FIG. 3. FIG. 3 is SDS-PAGE of the three major components (s-d, s-a and s-b) of sericin fractionated and purified.

The purities of sericins d, a and b became high and sericin a, which was expected to contain a little b, was estimated, from the SDS-PAGE, to have a purity of 90% or more.

EXAMPLE 2

[Cell Growth Promoting Action of Three Components of Sericin]

For three components of sericin, the presence of cell growth promoting action was checked using fibroblast cells derived from a normal human skin.

Fibroblast cells are dispersively present in almost all tissues in animal bodies and have a characteristic that when a trauma is added to the tissue or a parenchymal cell of an organ is lost, cells multiply by cell division to repair a missing part.

The three components of sericin fractionated and purified were dissolved in a 70% aqueous lithium thiocyanate solution and the resultant was subjected to dialysis with water.

Dialysis was carried out until the concentration of thiocyanate ion became 0.01 M or less and the bottom of a cell culture vessel of polystyrene (35 mmφ) was coated with the resultant solution.

The coating was carried out in a ratio of 25 micrograms/cm².

The vessel coated was washed with a physiological saline solution and then was sterilized by 70% ethanol, thereby being used as a cell culture vessel.

The number of 20,000 fibroblast cells derived from a normal human skin were suspended in 1 ml of cell culture liquid and 2 ml of the resulting liquid was inoculated in the cell culture vessel.

After a five-day culture, the number of cells was measured by the Alamar Blue dye method.

The results are shown in Table 2. Table 2 shows that sericin a promotes the growth of fibroblast cells. Sericins d and b were observed not to have cell growth promoting action.

TABLE 2

Action of promoting growth of fibroblast cells derived from a normal human skin of sericin components

| Test region | Growth (%) |
|---|---|
| Control (Polystyrene) | 100 ± 7.1 |
| s-a | 305 ± 10.2 |
| s-d | 95 ± 16.5 |
| s-b | 111 ± 7.3 |

EXAMPLE 3

[Cell Growth Promoting Action of a Material Containing Sericin a]

A cocoon layer of a domestic silkworm was kept in 8 M urea at 80° C. for 10 minutes, thereby being extracted.

To this extract of sericin was added alcohol, thereby precipitating sericin.

This precipitate comprises sericins d, a, b and c shown in FIG. 1.

This sericin precipitate was dissolved in a saturated aqueous lithium thiocyanate solution and, after desalting, was applied to the bottom of a cell culture vessel. The action of promoting growth of fibroblast cells derived from a normal human skin was investigated.

The procedures during the investigation were the same as those done in Example 2.

With respect to the action of promoting growth of fibroblast cells derived from a normal human skin cultured in culture beds containing any one component of sericin, the results are shown in Table 3.

As Table 3 shows, if a material contains sericin a, which has a cell growth promoting action, the material has a cell growth promoting action.

The sample in Table 3 contains the components of sericin (sericins d, a, b and c). However, if sericin a is contained, other sericins may be components of fibroin.

Further, components other than sericin a may be degraded.

Identification of sericin a is carried out based on the presence of a band of SDS-PAGE as shown in FIG. 1.

TABLE 3

Action of promoting growth of fibroblast cells derived from a normal human skin cultured in culture beds containing the components (s-d, s-a, s-b and s-c) of sericin

| Test region | Growth (%) |
|---|---|
| Control (Polystyrene) | 100 ± 8.3 |
| Precipitate containing the components of sericin | 172 ± 13.6 |

EXAMPLE 4

[Preparation of a Material Containing Sericin a in Silk Yarn]

Cocoon filaments are in a state where the surface of fibroin fibers is covered with sericin.

If sericin d is removed from the cocoon filaments, about 70% of sericin is accounted for by sericin a.

Here, a cocoon layer of a domestic silkworm was immersed in water the weight of which was 100 times the weigh of the cocoon layer and was boiled.

Figure 4:
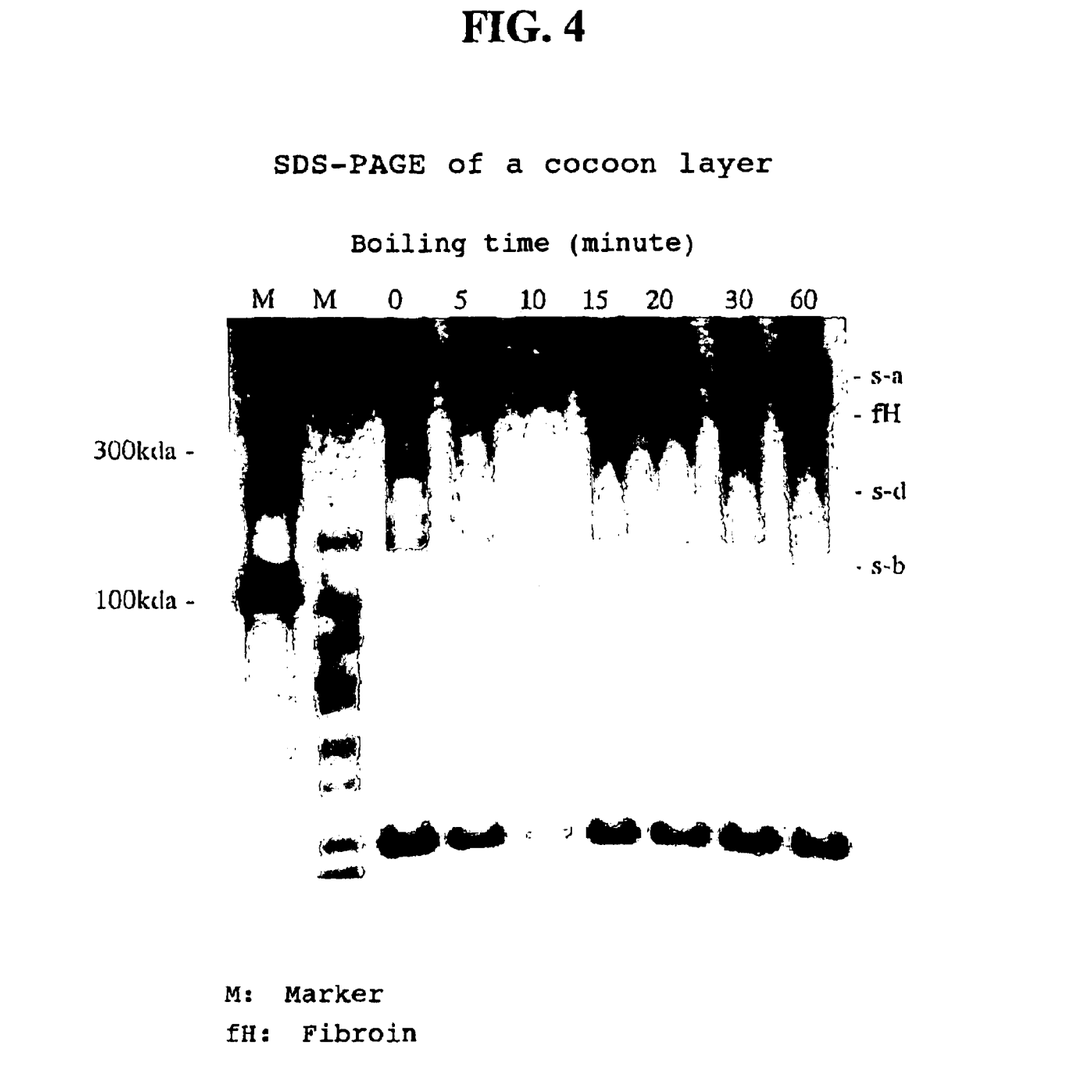
FIG. 4 is SDS-PAGE of a cocoon layer protein.

SDS-PAGE of cocoon layer proteins obtained by letting the boiling time be 5, 10, 15, 20, 30 and 60 minutes, respectively, are shown in FIG. 4.

After 20 minutes and 30 minutes, only sericin a and sericin c remain on the surface of a fibroin fiber, but after 15 minutes, a little sericin b also remains.

On the other hand, sericin a is difficult to leave the surface of cocoon filaments, but, after 60 minutes, the amount thereof is very small.

Further, a cocoon layer of a domestic silkworm was immersed in water the amount of which was 100 times the amount of the cocoon layer and 0.2 g of marseilles soap was added thereto and boiled.

The cocoon layer was treated by letting the boiling time be 5, 10, 15, 20, 30 and 60 minutes. The treatment time and sericin components on the surface of cocoon filaments were investigated by electrophoresis.

As a result, every components of sericin can be found in the cocoon layer, which is the raw silk material, but after 20 minutes and 30 minutes, only sericin a and sericin c remained on the surface of the fibroin fibers.

After 60 minutes, the amount of sericin a is very small.

Accordingly, if a cocoon layer is boiled in water or soapy water for about 10 to 60 minutes, preferably for about 15 to 40 minutes, almost all components present on the surface of the fibroin fibers can be sericin a.

EXAMPLE 5
[Degradation of Sericin]

A cocoon layer of a domestic silkworm was immersed in 8 M urea for 5 minutes, thereby extracting sericin.

This sericin extract was treated for 5, 10, 15, 20, 30 and 60 minutes at 100° C.

Figure 5:
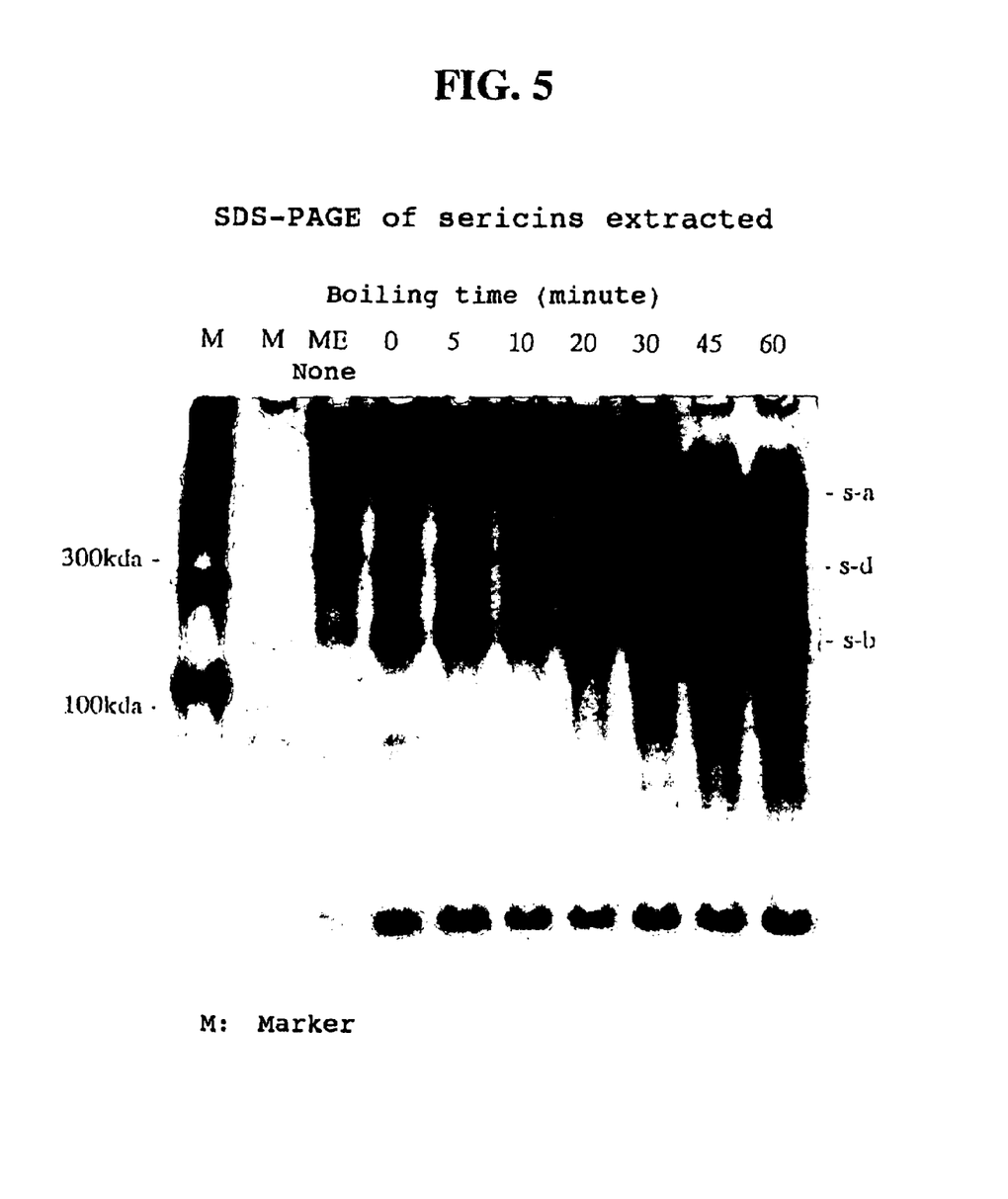
FIG. 5 is SDS-PAGE of sericins extracted.

FIG. 5 shows the SDS-PAGE of the cocoon filaments after the treatments.

Sericin a component is degraded faster than components d and b.

If the treatment time is 20 minutes, sericin a component can be detected clearly, but after a treatment of 30 minutes, the amount of sericin a component has become very small and after a treatment of 45 minutes, almost no sericin a component can be found.

FIG. 5 shows the SDS-PAGE of sericin extracted. A cocoon layer of a domestic silkworm was immersed in 8 M urea of 80° C. for 5 minutes, thereby extracting sericin. This sericin extract was treated for 5, 10, 15, 20, 30 and 60 minutes at 100° C.

EXAMPLE 6
[Animal Experiment]

In this example, the effect as a wound dressing material was investigated in detail using a hairless dog (NOSAN Corp.) As the wound dressing material used, a precipitate (a), obtained in Example 1 above, containing 90% or more of sericin a and a precipitate (S), obtained in Example 3, containing every components of sericin were used.

These precipitates were washed fully with water, freeze dried, and pulverized.

The average particle diameters of the powders are from 10 to 20 μm.

Further, a silk yarn (Fa) containing sericin a component obtained in Example 4 above by boiling a cocoon layer of a domestic silkworm in water for 15 minutes was also used in an animal experiment.

In this case, the silk yarn was cut into a yarn length of about 0.5 mm or less.

A film (L-S) containing sericin was prepared in the following manner from liquid silk.

When a domestic silkworm (Japanese 137×Chinese 137) has reached a time immediately before discharging yarns, the body of the silkworm was disinfected with alcohol. The silk gland was removed and washed with water. The liquid silk contained in the middle portion of the middle silk gland was removed and immersed in water.

The immersion solution obtained within 20 minutes of immersion was dried on a plastic plate at room temperature under ventilation to form a film 30 μm thick.

This film contains sericin in a content of about 70% and shows water-solubility.

In addition to the above, for comparison, a film (A-1) being 40 μm in thickness, comprising 1.7% of sericin and 98.3% of fibroin and showing a water-solubility was tested as a wound dressing material using a hairless dog.

This film (A-1) is that prepared via film forming procedures similar to those employed for a film A-1 shown in Table 4 of Example 3 in Japanese Patent No. 2990239 invented by the present inventor.

Further, a fibroin powder (F-1.8) [having an average particle diameter of 1.8 μm and showing a water-solubility] obtained by immersing a silk yarn in an aqueous sodium carbonate solution of 120° C. for two hours, washing with water, drying and then pulverizing was also tested as a wound dressing material using a hairless dog.

This fibroin powder is that produced under the same conditions as those under which the fibroin powder (3) shown in Table 4 of Example 3 in Japanese Patent Application No. Hei 11-259149 invented by the present inventor was prepared.

The case where no wound dressing material was used was employed as a control region.

First, skins in the back of a hairless dog from the cuticle to the dermis were removed each in a size of about 1 cm$^2$, and the wounds were disinfected with the disinfectant Hibitane, applied with a drop of benzylpenicillin procaine, which is an antibiotic for animals manufactured by MEIJI SEIKA KAISHA, LTD., and covered with each wound dressing material.

Further, the wound was covered with a polyurethane film with an absorbent pad, OpSite produced by Smith & Nephew.

Furthermore, a jacket for a dog was placed for the purpose of preventing the wound dressing material from falling off.
Observation On the days one week and two weeks after the start of the test, the test sites were observed and recorded.

The results are shown in Table 4.

In Table 4, a symbol "--" (no) appeared in an item "Amount of Exudate from Inflammatory Region" means a desirably cured condition, while a symbol "+++" (excellent) appeared in an item "Reproduction of Cuticle" (remarkable) means a remarkably cured condition.

All the wound dressing materials promoted the cure of a wound better than the control region and showed a curing effect. Sericin a component or wound dressing materials (a, s, Fa) containing the a component exhibited curing effects equal to or better than that exhibited by the amorphous fibroin film (containing 1.7% of sericin) A-1 used as comparison.

The curing effect of dressing materials S and A-1 are almost the same as shown in Table 4, but, in comparison of S and A-1, S had a curing effect better than that of A-1.

TABLE 4

Observation of Cure of Dressing Material with respect to Wound of Hairless Dog.

| Days after wounded | Condition of Tissue | a | S | Fa | L-S | A-1 | F-1.8 | Control Region |
|---|---|---|---|---|---|---|---|---|
| 7 days | Amount of Exudate from Inflammatory Region | -- | - | -- | -- | - | + | ++ |
|  | Reproduction of Cuticle | + | + | + | + | + | - | -- |
| 14 days | Amount of Exudate from Inflammatory Region | -- | -- | -- | -- | -- | - | + |
|  | Reproduction of Cuticle | +++ | ++ | ++ | ++ | ++ | ++ | + |

--: no, -: scarce, +: some, ++: medium, +++: remarkable

Industrial Applicability

Since the above-described cell growth promoter produced by the present invention has an effect of promoting growth of cells, it can be used widely in various fields in which the cell growth promoter can be expected, for example, in a wound dressing material, a vascular endothelium forming material and an organ forming material for medical use, in a cell culture base material for biological use, or in a cosmetic material for skin care use.

We claim:

1. A cell growth promoter obtainable by elution from a fiber discharged by a domestic silkworm (cocoon filaments or the like) wherein the cell growth promoter comprises sericin having a molecular weight of about 400,000 as measured by sodium dodecyl sulfate-polyacrylamide gel electrophoresis (SDS-PAGE) as a main component.

2. A method comprising dissolving sericin contained in a fiber discharged by a domestic silkworm (cocoon filaments or the like) in an aqueous urea solution, and then separating and recovering sericin having a molecular weight of about 400,000 as measured by sodium dodecyl sulfate-polyacrylamide gel electrophoresis (SDS-PAGE).

3. The method for separating and recovering according to claim 2, wherein sericin is dissolved in an aqueous urea solution of a concentration of 4 M or more.

4. A cell growth promoter obtainable by dissolving a fiber discharged by a silkworm (cocoon filaments or the like) in an aqueous solution of a neutral salt, wherein the cell growth promoter contains silk fibroin and sericin having a molecular weight of about 400,000 as measured by sodium dodecyl sulfate-polyacrylamide gel electrophoresis (SDS-PAGE).

5. The cell growth promoter according to claim 1, wherein the call growth promoter having in the form of a powder or a film.

6. A cell growth promoter obtainable by scouring a fiber discharged by a domestic silkworm (cocoon filaments or the like) under mild conditions and removing sericin having a low molecular weight, wherein the cell growth promoter comprises a fibrous material in a state where the surface of a fibroin filament is covered with a sericin component having a molecular weight of about 400,000 as measured by sodium dodecyl sulfate-polyacrylamide gel electrophoresis (SDS-PAGE).

7. A method for producing a fibrous material in a state where the surface of a fibroin filament is covered with a sericin component having a molecular weight of about 400,000 as measured by sodium dodecyl sulfate-polyacrylamide gel electrophoresis (SDS-PAGE), the method comprising scouring a fiber discharged by a domestic silkworm (cpcoon filaments or the like) under mild conditions and removing sericin having a low molecular weight.

8. The method for producing a fibrous material according to claim 6, wherein scouring by boiling is conducted within a mild pH range as close to neutrality as possible.

9. A cell growth promoter obtainable by immersing a liquid silk contained in the middle silk gland and the anterior silk gland in the body of a silkworm, wherein the cell growth promoter comprises sericin having a molecular weight of about 400,000 as measured by sodium dodecyl sulfate-polyacrylamide gel electrophoresis (SDS-PAGE) as a substantial main component.

10. A method of using the cell growth promoter according to claim 1 for a cosmetic material as a skin care material; a wound dressing material, a material for vascular endothelium formation and a material for organ formation as a medical material, and a cell culture bed material as a biological material.

* * * * *